US011744527B2

(12) United States Patent
Scott et al.

(10) Patent No.: US 11,744,527 B2
(45) Date of Patent: Sep. 5, 2023

(54) DETERMINATION AND VISUALIZATION OF ANATOMICAL LANDMARKS FOR INTRALUMINAL LESION ASSESSMENT AND TREATMENT PLANNING

(71) Applicant: KONINKLIJKE PHILIPS N.V., Eindhoven (NL)

(72) Inventors: Jeff Scott, Cardiff, CA (US); Pei-Yin Chao, Eindhoven (NL)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 645 days.

(21) Appl. No.: 16/354,970

(22) Filed: Mar. 15, 2019

(65) Prior Publication Data
US 2019/0282182 A1 Sep. 19, 2019

Related U.S. Application Data

(60) Provisional application No. 62/643,366, filed on Mar. 15, 2018.

(51) Int. Cl.
*A61B 5/00* (2006.01)
*A61B 8/12* (2006.01)
(Continued)

(52) U.S. Cl.
CPC .......... *A61B 5/7425* (2013.01); *A61B 5/0073* (2013.01); *A61B 5/0084* (2013.01); *A61B 5/02007* (2013.01); *A61B 8/0891* (2013.01); *A61B 8/12* (2013.01); *A61B 8/463* (2013.01); *A61B 8/466* (2013.01); *A61B 8/5261* (2013.01);
(Continued)

(58) Field of Classification Search
None
See application file for complete search history.

(56) References Cited

U.S. PATENT DOCUMENTS

| 2011/0071404 A1 | 3/2011 | Schmitt | |
| 2014/0276085 A1* | 9/2014 | Miller | A61B 8/483 |
| | | | 600/467 |

(Continued)

FOREIGN PATENT DOCUMENTS

| WO | 2016187231 A1 | 11/2016 | |
| WO | WO-2016187231 A1 * | 11/2016 | .......... A61B 5/0066 |
| WO | 2018064336 A1 | 4/2018 | |

OTHER PUBLICATIONS

"Systems Devices and Methods for Displaying Multiple Intraluminal Images in Luminal Assessment With Medical Imaging", U.S. Appl. No. 62/711,927, filed Jul. 30, 2018.

(Continued)

*Primary Examiner* — Colin T. Sakamoto
*Assistant Examiner* — Marjan Saboktakin

(57) ABSTRACT

Systems, devices, and methods are provided to determine and visualize landmarks with an intraluminal imaging system for lesion assessment and treatment. An intraluminal imaging system may be configured to receive imaging data from an intraluminal imaging device, generate a set of image frames using received imaging data, and automatically calculate a luminal area associated with the body lumen for each of the image frames. The calculated luminal area and a longitudinal view of the body lumen may be displayed to a user on a display device.

21 Claims, 12 Drawing Sheets

(51) Int. Cl.
| | |
|---|---|
| *A61B 8/08* | (2006.01) |
| *A61B 8/00* | (2006.01) |
| *A61B 5/02* | (2006.01) |
| *A61B 34/10* | (2016.01) |
| *A61B 34/00* | (2016.01) |
| *A61F 2/07* | (2013.01) |

(52) U.S. Cl.
CPC .............. *A61B 34/10* (2016.02); *A61B 34/25* (2016.02); *A61B 2034/107* (2016.02); *A61F 2/07* (2013.01)

(56) References Cited

U.S. PATENT DOCUMENTS

| | | |
|---|---|---|
| 2015/0073279 A1 | 3/2015 | Cai |
| 2015/0297373 A1 | 10/2015 | Schmitt |
| 2016/0157808 A1* | 6/2016 | Merritt ................ A61B 5/0035 600/427 |
| 2016/0206267 A1 | 7/2016 | Shimizu |

OTHER PUBLICATIONS

"Scoring Intravascular Lesions and Stent Deployment in Medical Intraluminal Ultrasound Imaging", U.S. Appl. No. 62/643,105, filed Mar. 14, 2018.

"Hard Shell Roof-Top Tent With Utility Rails", U.S. Appl. No. 62/351,175, filed Jun. 16, 2016.

"Intravascular Imaging Procedure-Specific Workflow Guidance and Associated Devices Systems and Methods", U.S. Appl. No. 62/712,009, filed Jul. 30, 2018.

* cited by examiner

DETERMINATION AND VISUALIZATION OF ANATOMICAL LANDMARKS FOR INTRALUMINAL LESION ASSESSMENT AND TREATMENT PLANNING

TECHNICAL FIELD

The present disclosure relates generally to obtaining intravascular data associated with a body lumen of a patient, and, in particular, to determining and visualizing landmarks with an intraluminal imaging system for lesion assessment and treatment.

BACKGROUND

Various types of intraluminal (also referred to as intravascular) imaging systems are used in diagnosing and treating diseases. For example, intravascular ultrasound (IVUS) imaging is widely used in interventional cardiology as a diagnostic tool for visualizing vessels within a body of a patient. This may aid in assessing vessels, such as an arteries, veins, and other lumens within the human body to determine the need for treatment, to optimize treatment, and/or to assess its effectiveness.

In some cases, intraluminal imaging is carried out with an IVUS device including one or more ultrasound transducers. The IVUS device may be passed into the vessel or artery and guided to an area of interest to be imaged. The transducers emit ultrasonic energy and receive ultrasound echoes reflected from the vessel. The ultrasound echoes are processed to create one or more images of the area of interest. The images of the areas of interest may include one or more lesions or blockages in the vessel. One or more stents may be placed within the vessel or artery to treat these lesions and intraluminal imaging may be carried out to view the placement of the stent within the vessel.

In imaging analysis of the intraluminal images, it may be useful to judge the severity of a lesion within the vessel or artery by generating and displaying measurements that correspond to landmarks. These landmarks may assist in treatment planning. To identify these landmarks in existing intraluminal imaging systems, a medical professional manually selects and marks imaging data to identify landmarks. In particular, the medical professional may select a single frame of imaging data, inspect the frame, manually select a number of points on the image (such as around a tissue border in the image) with an input device, and calculate the dimensions of the area within the points to determine a vessel or lumen area. The medical professional may then proceed to another frame and repeat the same process. Through analysis of these manually marked areas, the medical professional may be able to estimate the extent and severity of a lesion within the lumen.

However, because many frames may be analyzed, requiring a high level of expertise, this process can be time consuming and costly. Furthermore, existing intraluminal imaging systems may lead to logistical and judgment errors because of confusion between the many frames that are analyzed and the difficulty in scrolling through the frames to identify a lesion. This may cause the medical professional to completely miss a lesion or misjudge the extent of the lesion. Thus, deficiencies exist in current intraluminal image systems for identifying landmarks and assessing lesions.

SUMMARY

Systems, devices, and methods for identifying landmarks in a lumen and assessing a blockage within a body lumen (e.g., a lesion within a blood vessel) are provided. In particular, the intraluminal imaging system may provide automated identification and measurement of landmarks, areas of interest, and lesions within the lumen. These measurements may be displayed with intraluminal images and may be used to recommend further imaging or treatment procedures. Aspects of the present disclosure advantageously provide intraluminal landmark identification and measurement that overcome the limitations of existing intraluminal imaging systems.

Embodiments of the present disclosure provide an intraluminal medical imaging system, which may include: a controller in communication with an intraluminal imaging device configured to be positioned within a body lumen of a patient, the controller configured to: receive imaging data from the intraluminal imaging device as it is moved through the body lumen of the patient; generate a set of image frames using the received imaging data; automatically calculate a luminal area associated with the body lumen for each of the image frames; and a display device in communication with the controller and configured to display, on a single screen, a first image frame of the set of image frames, the calculated luminal area corresponding to the first image frame, and a longitudinal view of the body lumen.

In some embodiments, the first image frame is a two-dimensional tomographic image of the body lumen. The display device may be further configured to display a hybrid two-dimensional/three-dimensional image including the first image frame and a depiction of a portion of the body lumen extending from the first image frame. A location of the first image frame within the body lumen may be displayed on the longitudinal view of the body lumen. The display device may be further configured to display an area of interest including a lesion.

In some embodiments, the display device is further configured to display, on the single screen, a percentage of narrowing of the body lumen within the area of interest. The controller may be further configured to automatically determine an optimal location for a stent based on the received image data. The display device may be further configured to display the optimal location on the longitudinal view of the body lumen.

A method of intraluminal medical imaging is also provided, which may include: receiving, with a controller in communication with a intraluminal imaging device positioned within a body lumen of a patient, imaging data associated with the body lumen; generating, with the controller, a set of image frames using the received imaging data; automatically calculating, with the controller, a luminal area of each of the image frames; and displaying, on a single screen of a display device, a first image frame of the set of image frames, the calculated luminal area corresponding to the first image frame, and a longitudinal view of the body lumen.

In some embodiments, the first image frame is a two-dimensional tomographic image of the body lumen. The method may include displaying, on the display device, a hybrid two-dimensional/three-dimensional image including the first image frame and a depiction of a portion of the body lumen extending from the first image frame. A location of the first image frame within the body lumen may be displayed on the longitudinal view of the body lumen. The method may include displaying, on the single screen of the display device, an area of interest within the body lumen including a lesion.

In some embodiments, the method may include displaying, on the single screen of the display device, a percentage of narrowing of the body lumen within the area of interest. The method may include determining, with the controller, an optimal location for a stent based on the received image data. The method may include comprising displaying the optimal location on the longitudinal view of the body lumen.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
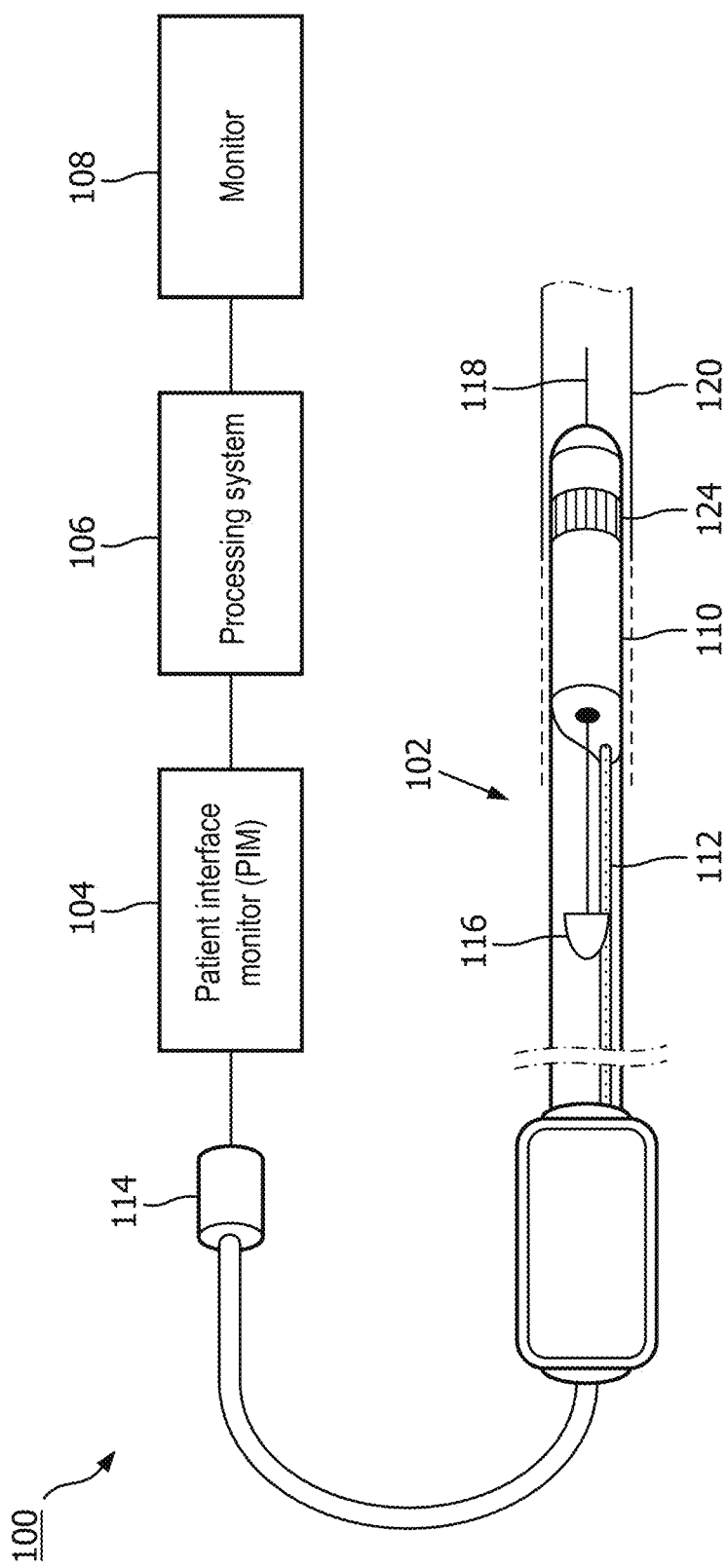
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, and a monitor 108. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. In some embodiments, the intraluminal imaging system 100 is configured to automatically identify and measure landmarks within a lumen, such as tissue borders, areas of interest, and lesions. These measurements may assist a user in visualizing the lumen, as well as recommending further imaging or treatment procedures.

The devices, systems, and methods described herein can include one or more features described in U.S. Provisional App. No. 62/643,105, filed on Mar. 14, 2018, U.S. Provisional App. No. 62/642,847, filed on Mar. 14, 2018, U.S. Provisional App. No. 62/712,009, filed on Jul. 30, 2018, and U.S. Provisional App. No. 62/711,927, filed on Jul. 30, 2018, each of which is hereby incorporated by reference in its entirety.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 can include an imaging component of any suitable imaging modality, such as optical imaging, optical coherence tomography (OCT), etc. In some embodiments, the device 102 can include any suitable imaging component, including a pressure sensor, a flow sensor, a temperature sensor, an optical fiber, a reflector, a mirror, a prism, an ablation element, a radio frequency (RF) electrode, a conductor, and/or combinations thereof. Generally, the device 102 can include an imaging element to obtain intraluminal data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, and monitor 108 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, the intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducers between 1 transducer and 1000 transducers, including values such as 2 transducers, 4 transducers, 36 transducers, 64 transducers, 128 transducers, 500 transducers, 812 transducers, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, select particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

In some embodiments, the IVUS data and/or the external ultrasound data may be co-registered with the 2D or 3D CT image, which may further improve placement accuracy and decrease procedural time. The placement of the intraluminal device 102 may be verified with this multi-imaging system, which may improve outcomes versus standard fluoroscopic guidance. In some embodiments, the intraluminal device 102 is tracked to the target location as identified on a CT image and/or angiogram (such as a lesion or aneurysm). In some embodiments, a roadmap produced from co-registered IVUS and CT image data may be correlated to fluoroscopic data to further improve accuracy. For example, the processing system 106 may create an imaging loop based on the roadmap and fluoroscopic data to improve the navigation of the intraluminal device 102 through the vessels of the patient.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or surrounded structures, both natural and man-made. Lumen 120 may be within a body of a patient. Lumen 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the processing system 106 may be configured to automatically measure landmarks or key luminal areas within a lumen. These landmarks may include borders of tissue layers (such as a lumen or vessel border). The dimensions of these landmarks may be automatically measured by the processing system 106. These measurements may be displayed on one or more images of the lumen. In some embodiments, the measurements may be used to identify lesions within the lumen and determine the severity and extent of these lesions. The identification and measurement these landmarks may a user to easily visualize a lumen within the patient and accurately assess the severity and extent of lesions therein. This may add confidence to the assessment of lesions and save time in measurement procedures.

In some embodiments, the intraluminal device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intraluminal device 102 my include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as checking on a stent that has been positioned in a lumen. The workflow may be presented to a user as any of the displays or visualizations shown in FIGS. 2-7.

Figure 2:
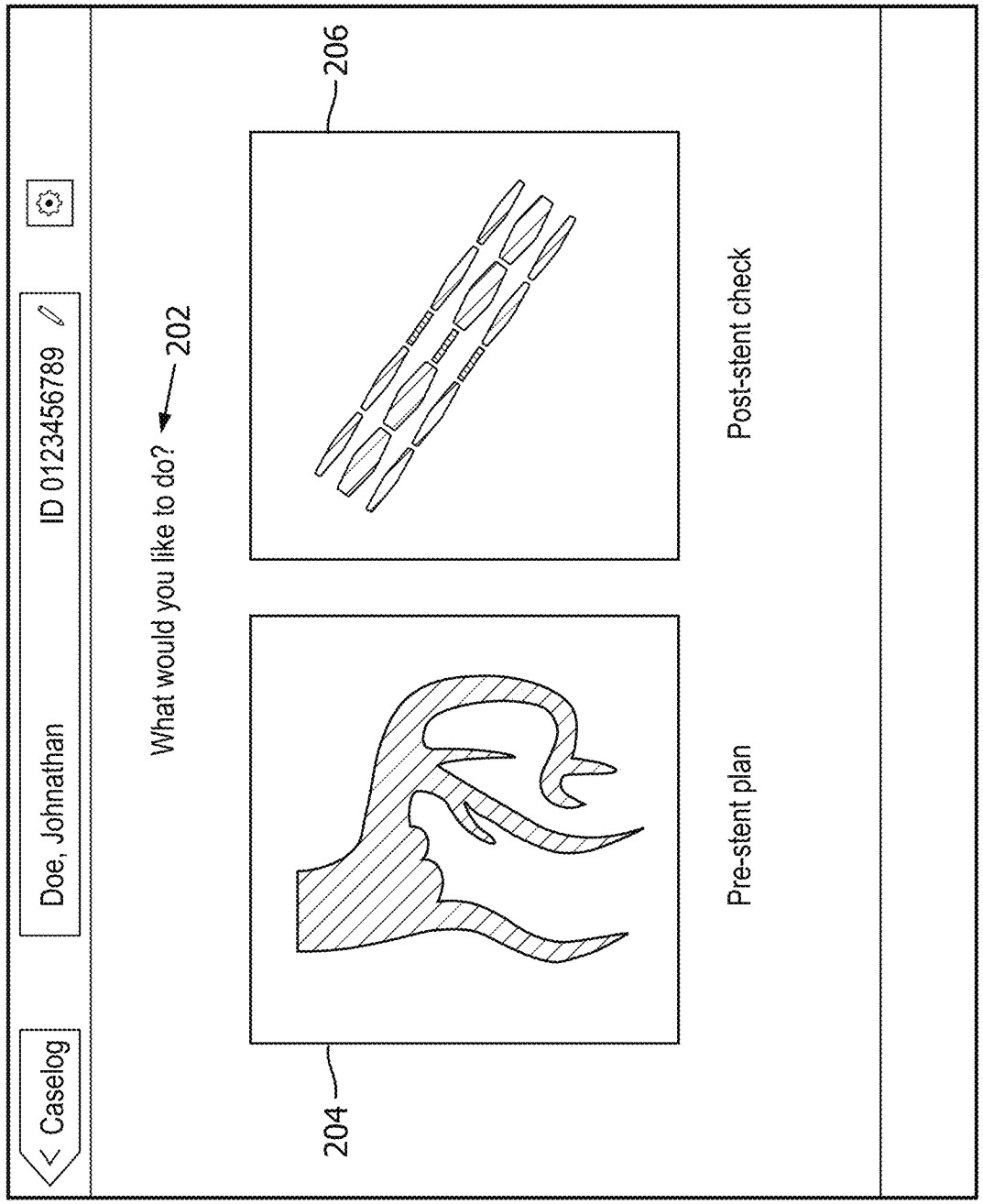
FIG. 2 is an exemplary illustration of a display showing a prompt according to aspects of the present disclosure.

FIG. 2 shows an exemplary display 200 showing a prompt 202 according to aspects of the present disclosure. In some embodiments, the display 200 is displayed on the monitor 108 as shown in FIG. 1. In other embodiments, the display 200 is displayed on a screen of another device, such as PIM 104. The display 200 may be generated by a controller of the intraluminal imaging system 100. In some embodiments, the display 200 is configured to display prompts and instructions as well as other data to an operator. The display 200 may be used to show a complete end-to-end workflow for an intraluminal procedure. This workflow may include a number of prompts and instructions that may guide an operator through a procedure. This may simplify the steps of a procedure and help to avoid operator errors.

Figure 3:
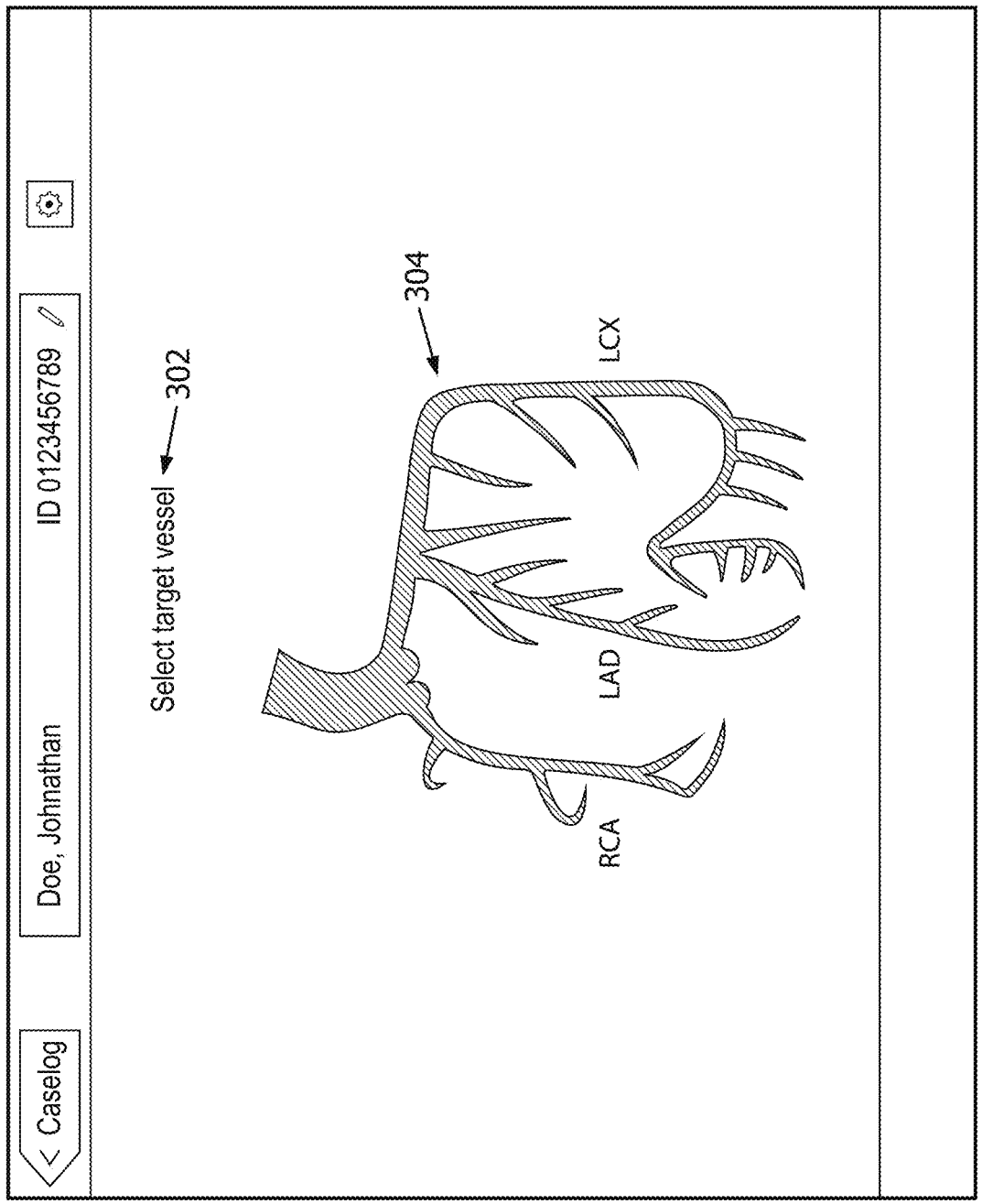
FIG. 3 is an exemplary illustration of a display showing another prompt according to aspects of the present disclosure.

The prompts and instructions may be displayed on the display 200 as selectable options such that an operator may interact with the display 200 to choose options. The selections of the operator may change the display 200 such that information corresponding with the selected options is shown. In the example of FIG. 2, a selectable prompt 202 is displayed on display 200. The prompt includes two selectable options: option 204 corresponds to a pre-stent plan and option 206 corresponds to a post-stent check. The operator may select one of the options 204, 206 which may move the workflow forward, such that other screens are displayed (such as prompt 302 as shown in FIG. 3). The options 204, 206 may include visual representations of the type of procedure. For example, option 204 may include a depiction of vasculature within the heart and option 206 may include a depiction of a stent. In some embodiments, a change in the visual depiction of the option 204, 206 may show a preference for a certain type of procedure. For example, the option 204 may appear as shaded or grey if the system determines that the option 204 is not suited to the procedure at hand. In other embodiments, the selection of an option 204, 206 may involve a change in the visual depiction of the option 204, 206. For example, if the pre-stent plan option 204 is selected, the option 204 may appear as shaded or grey in future displays of the display 200. This may help to indicate that this option 204 has previously been selected by an operator. Other types of feedback may be used to indicate selections of options. For example, the selectable options 204, 206 may display blinking areas, highlighted areas, altered colors, shading, altered transparencies, and other visual indicators.

Option 204 may provide a tailored workflow for a pre-stent plan that may include performing an intraluminal procedure (such as a pullback operation) and viewing automated results. Option 204 may be used to identify areas within a lumen 120 that may benefit from the placement of a stent. Option 206 may provide a tailored workflow for a post-stent check that may include performing an intraluminal procedure (such as a pullback operation) and viewing relevant results of an area within a lumen 120 where a stent has been placed (such as an edge dissection or a malapposition). This option 206 may be used to observe the placement and effectiveness of the stent.

FIG. 3 shows an exemplary display 200 showing a prompt 302 according to aspects of the present disclosure. In some embodiments, the prompt 302 may be displayed after either of the options 204, 206 are selected. In other embodiments, the prompt 302 is displayed only after the pre-stent plan option 204 is selected. The prompt 302 may prompt the operator to select a target vessel. In the example of FIG. 3, selecting the target vessel includes selecting a region on a visualization 304 including arteries in the heart. The selectable regions may include the right coronary artery (RCA), left anterior descending (LAD), and left circumflex artery (LCX). The selectable regions may also include various regions of the arteries, as well as other vessels and lumens within other parts of the anatomy of a patient. The appearance of the visualization 304 may be altered when one of the regions is selected by the operator. For example, the selected artery may be outlined, highlighted, or colored with a different color. In some embodiments, the selected artery is outlined in blue, as shown in FIG. 4.

Figure 4:
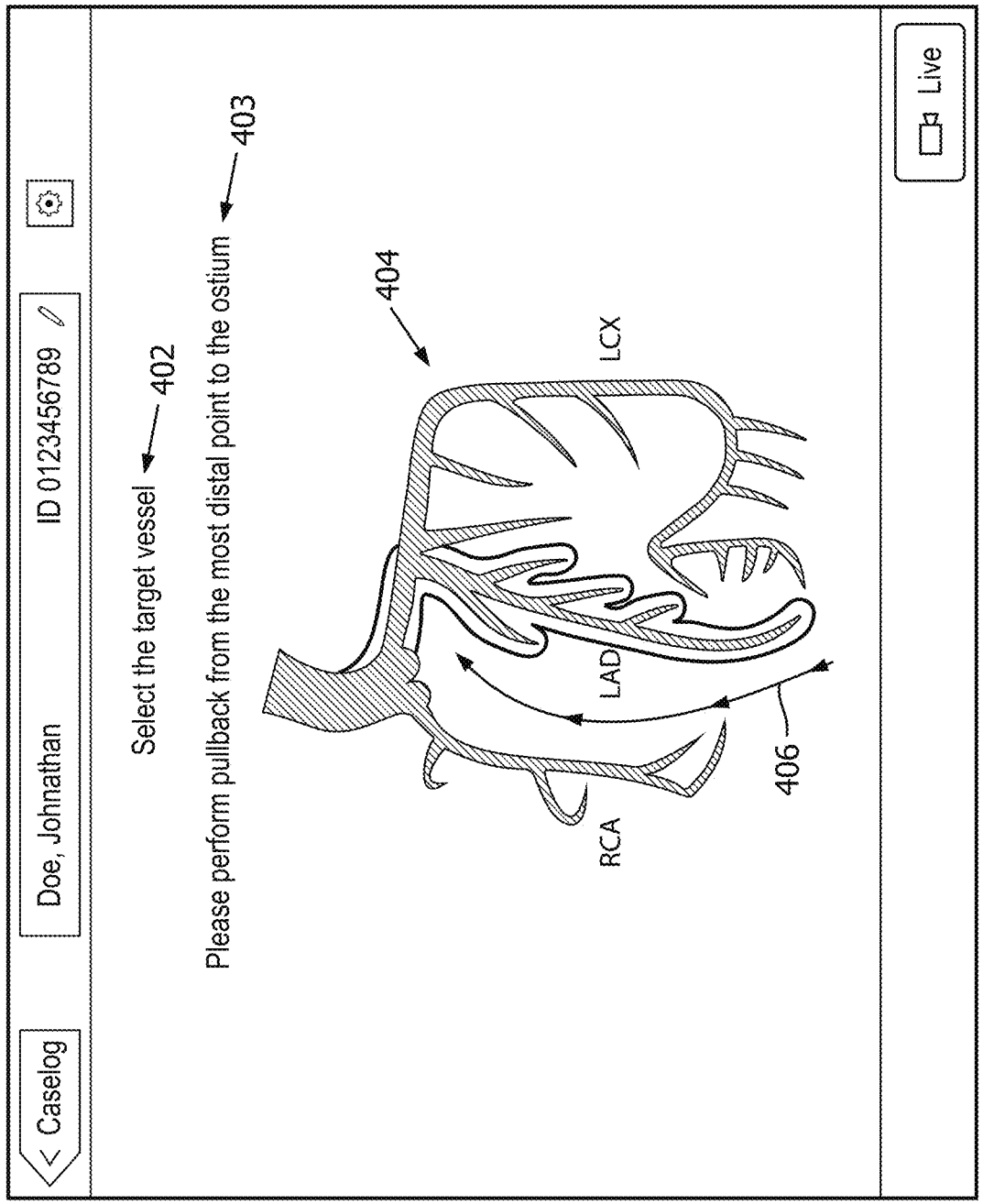
FIG. 4 is an exemplary illustration of a display showing another prompt and instructions according to aspects of the present disclosure.

FIG. 4 shows an exemplary display 200 showing a prompt 402 according to aspects of the present disclosure. The prompt 402 may be displayed after the operator has made a selection on the prompt 302 shown in FIG. 3. In the example of FIG. 4, the LAD artery has been selected by an operator. The prompt 402 shows the outlined image of the LAD along with instructions 403 to perform a pullback procedure from the most distal point on the LAD to the ostium. These instructions 403 may refer to a pullback procedure or other movement of the device 102 within the selected vessel or lumen 120. The instructions 403 may instruct an operator to perform any type of movement of the device 102 within a selected target vessel. For example, the instructions 403 may instruct an operator to push the device 102 a given distance along the selected target vessel. A visualization 404 corresponding to the instructions 403 may also be displayed on the display 200. In the example of FIG. 4, the visualization 404 includes a blue line 406 with arrows showing the direction in which the pullback procedure should be performed. The visualization 404 may include visual effects such as changing colors or animation. For example, the arrows of the visualization 404 may move in the direction specified by the instructions 403. The instructions 403 and visualization 404 may vary depending on options that were previously selected. For example, if an operator selected the RCA as the target vessel, the visualization 404 of the RCA would be highlighted and a corresponding visualization would be displayed showing a procedure outlined by instructions 403.

In some embodiments, the instructions 403 of the display 200 may vary depending on which option 204, 206 was selected from the prompt 202 shown in FIG. 2. For example, if the post-stent check option 206 was selected, the instructions may read "please perform pullback from the distal point of the stent to the proximal point of the stent." Other instructions may also be included to guide the operator to perform an imaging procedure and acquire imaging data relevant to the selected target vessel and/or stent.

Figure 5:
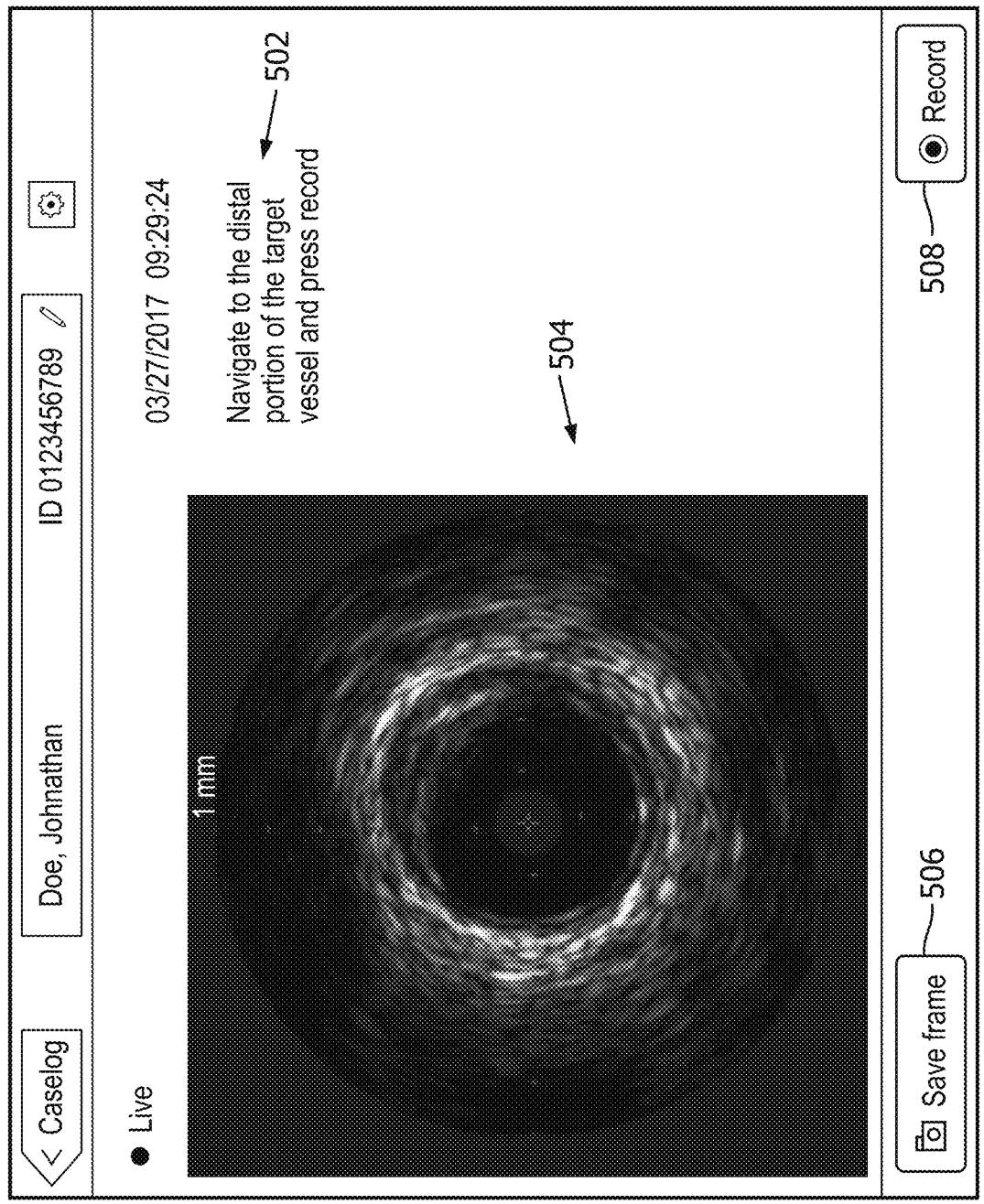
FIG. 5 is an exemplary illustration of a display showing imaging data and instructions according to aspects of the present disclosure.

FIG. 5 shows an exemplary display 200 showing a prompt 502 according to aspects of the present disclosure. The prompt 502 may be displayed after the operator has made a selection on the prompt 402 shown in FIG. 4. In the example of FIG. 5, the LAD artery has been selected by an operator. The prompt 502 may be accompanied by a visualization 504. In some embodiments, the visualization 504 shows imaging data from the device 102 as the device 102 is moved through the selected target vessel. The imaging data may be used as a reference for the operator. In particular, imaging data shown in the visualization 504 may help the operator to know where to begin a procedure. In the example of FIG. 5, the imaging data may show when the device 102 is positioned at a distal end of the LAD artery so that a pullback operation may be performed. The imaging data may also show other reference data such as areas of interest along a lumen 120, branches of the lumen 120, problem areas within the lumen 120, and other features. In some embodiments, when the device 102 is placed at the location specified by the instructions (for example, at a distal portion of an artery), the operator may select the record button 508 to begin a recording of the procedure. The display may also include an option 506 to save specific frames of imaging data before or during a procedure.

Figure 6:
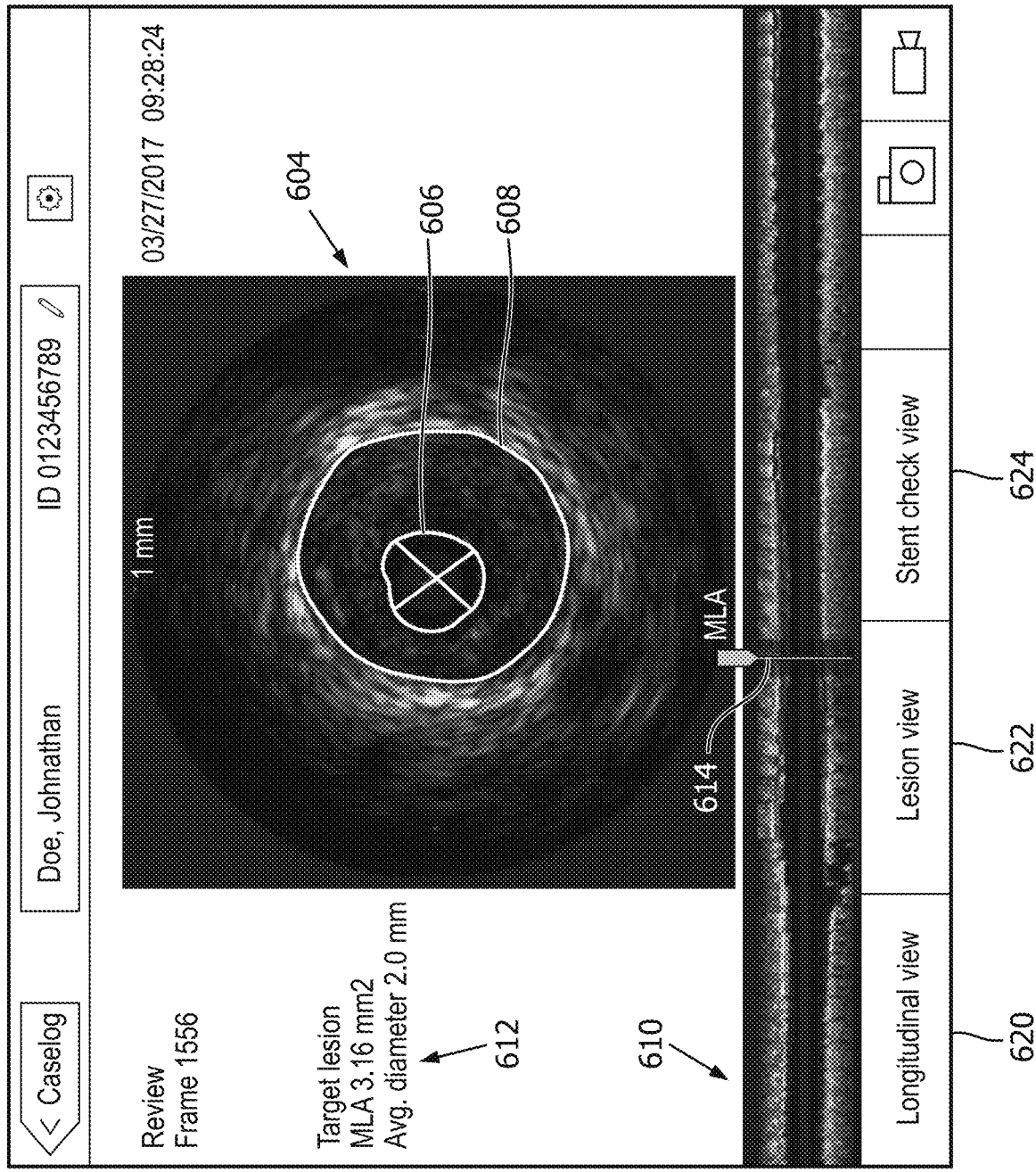
FIG. 6 is an exemplary illustration of a display showing imaging data according to aspects of the present disclosure.

FIG. 6 shows an exemplary visualization 310 according to aspects of the present disclosure. The visualization 310 may be displayed on a monitor 108. The visualization 310 may present imaging data acquired by the device 102 during an intraluminal procedure. In some embodiments, the intraluminal procedure is outlined in the instructions shown in FIGS. 3-5. In some embodiments, the visualization 310 includes imaging data corresponding to a lumen 120, such as the selected target vessel. The visualization 310 may include a first view 604 and a second view 610 of the lumen 120. In some embodiments, the first and second views 604, 610 may be oriented 90 degrees apart. In the example of FIG. 6, the first view 604 shows imaging data corresponding to a view straight down the lumen 120 (otherwise discussed as a "longitudinal view") and the second view 610 shows imaging data corresponding to a transverse view of the lumen 120. The views 604, 610 may include corresponding imaging data. The display of the first view 604 and second view 610 is not shown in this manner in existing systems. In some embodiments, the first view 604 and the second view 610 are automatically chosen by the system to highlight important aspects of the image, such an MLA, landing spot, stent border, or other feature of interest, such that the first view 604 and the second view 610 display these features in a simple graphical way to the user. Other views may also be shown, including one or more transverse, cross-sectional, and tomographic images.

In some embodiments, the visualization 310 may include a selected frame of imaging data received by the device 102. The operator may be able to select any frame from the imaging data received by the device 102. This may allow the operator to focus on specific areas of interest in the lumen 120.

In some embodiments, measurements are performed automatically on the imaging data with a controller of the intraluminal imaging system 100 as the imaging data is acquired by the device 102. Existing imaging systems typically require an operator to manually select a frame of interest and mark areas for measurement. This may be a time-consuming process, and may introduce user errors and require a high level of expertise, especially in marking areas for measurement. These errors may cause operators to miss important features within the imaging data, such as lesions. The intraluminal imaging system 100 provides automated measurement of features in received imaging data without requiring user interaction. In some embodiments, the system 100 may automatically measure all applicable boundaries in the imaging data (including on a displayed image), including anatomical boundaries (such as lumen boundaries, vessel boundaries, lesion boundaries, aneurism boundaries, and other tissue layer boundaries) and stents. Furthermore, the system 100 may automatically identify areas of interest based on the automatic measurements and display these areas of interest, correlated to a longitudinal view or angiographic image of the lumen. This automatic measurement, analysis, and display may provide an easy to understand overview of the condition of the vessel or arty of the patient, as well as providing data for determining the severity and extent of lesions therein.

In the example of FIG. 6, automatic measurements corresponding to a vessel boundary 608 and a minimum lumen area (MLA) 606 are displayed on the first view 604. The measurements may include lumen or vessel diameter, lumen or vessel area, lumen or vessel eccentricity, center measurements of the lumen or vessel, lumen or vessel boundary thickness, and other measurements performed automatically by the controller. These measurements may also be shown on other views. For example, a marker 614 is placed at the MLA in the second view 610 that corresponds with the lumen border 606 of the MLA in the first view 604. This may help an operator to visualize the diameter of vessel boundaries along the lumen 120. The measurements may be displayed in numerical format at box 612 on the visualization 310. Specific portions and views of the visualization 300 may be viewed by an operator by selecting the options 620, 622, and 624.

Measurements and/or metrics corresponding to the imaging data may be performed automatically by the intravascular imaging system and displayed by the visualization 300. For example, the intraluminal imaging system 100 may be used to perform length measurements such as minimum, maximum, average, and mean lengths of features in the imaging data. The effective diameter of features may also be measured. Area measurements of features such as lumens, vessels, plaque, and thrombus may be performed by the intraluminal imaging system 100. The measurements may include plaque burden, percent stenosis, percent difference, diameter stenosis, percent diameter stenosis, luminal gain, and luminal gain percentage. Furthermore, features of a stent may also be measured by the intraluminal imaging system 100, including overall stent area, minimum stent area, average stent area, stent apposition, expansion, malapposition, and a stent score. The visualization 300 can include numerical values of one or more of these measurements or other graphical representations (e.g., shading, coloring, etc.), including graphical representations overlaid on or displayed separately/spaced from tomographic, longitudinal, and/or angiographic images of a vessel.

Figure 7:
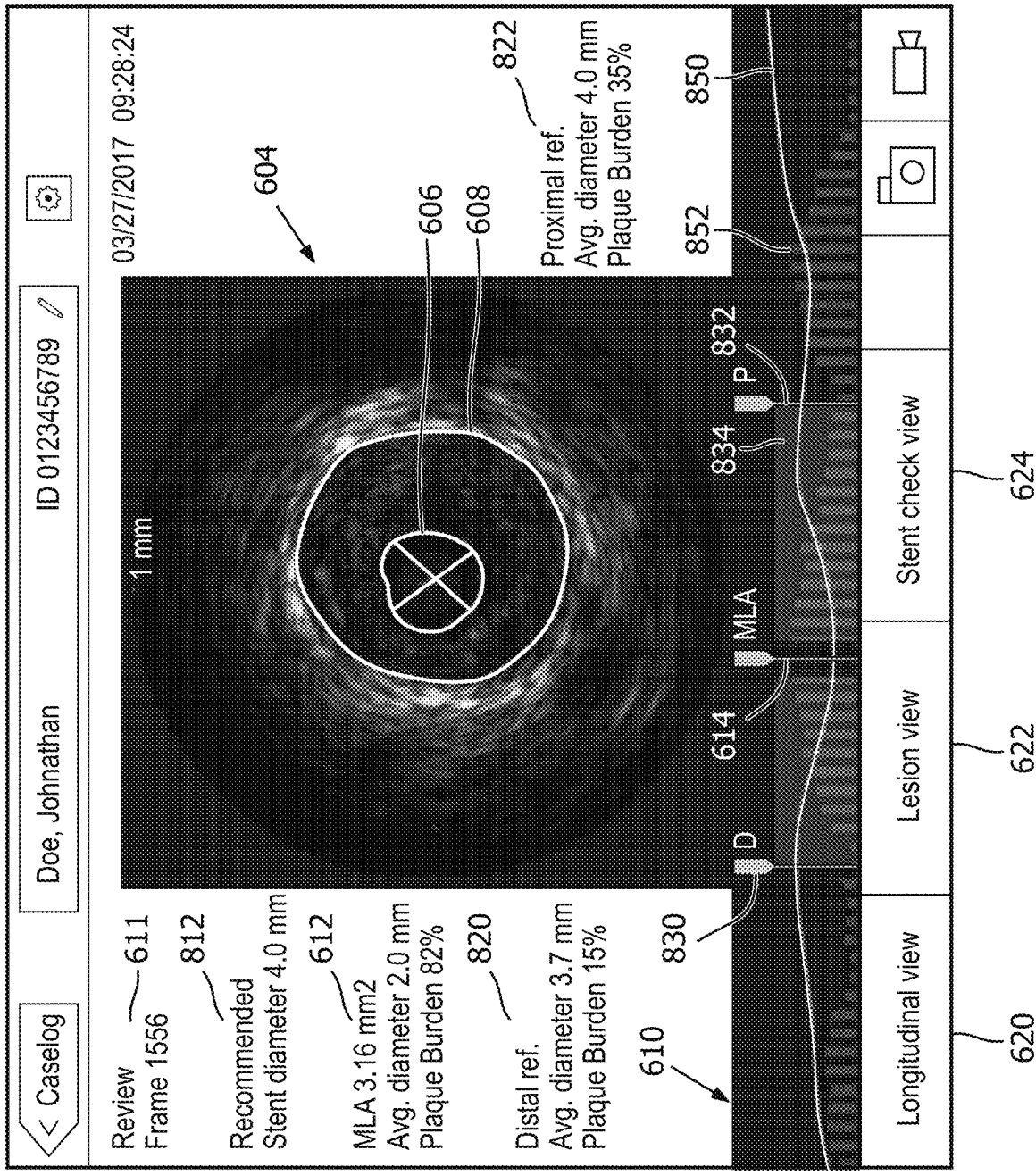
FIG. 7 is an exemplary illustration of a display showing various views of imaging data according to aspects of the present disclosure.

FIG. 7 shows an exemplary visualization 700 showing a lesion view according to aspects of the present disclosure. In some embodiments, visualization 700 corresponds to the pre-stent plan option 204 as shown in FIG. 2. In some embodiments, the visualization 700 may be used to recommend the placement and size of a stent to address a lesion. These recommendations may be made automatically by the system 100 based on the imaging data received by the device 102. In particular, the visualization 700 may be used to visualize a portion of a lumen 120 with a potential "landing spot" 834 for a stent. In some embodiments, the landing spot 834 is an area of interest within the lumen 120 that includes an MLA of a portion of the lumen 120, as marked by marker 614. The landing spot 834 may mark an area of the lumen recommended for treatment, such as placing a stent or positioning a balloon. The landing spot 834 may be automatically recommended by the system 100 based on the received imaging data received by the device 102. The landing spot 834 may be shown in profile in view 610 to show the potential placement of the stent within the landing spot 834. A distal end marker 830 and a proximal end marker 832 of the landing spot 834 may define the recommended placement of a distal and proximal edge of a stent to be placed in the lumen. The distal end marker 830 and proximal end marker 832 may be accompanied with numerical data 820, 822 illustrating the average diameter and plaque burden of the lumen 120 at these locations. In some embodiments, the visualization may also a depiction of the plaque burden 852 along the lumen 120. In some embodiments, the depiction of the plaque burden 852 is automatically measured based on imaging data from the device 102. The visualization 700 may also include a depiction of lumen area 850. As illustrated in FIG. 7, the marker 614 for the MLA may be placed where the plaque burden is the greatest and the area of the lumen is the smallest.

In some embodiments, the visualization 700 includes a recommended stent diameter as shown in text box 812. This diameter may be based on the diameter of the lumen 102 as measured by the system 100.

Figure 8:
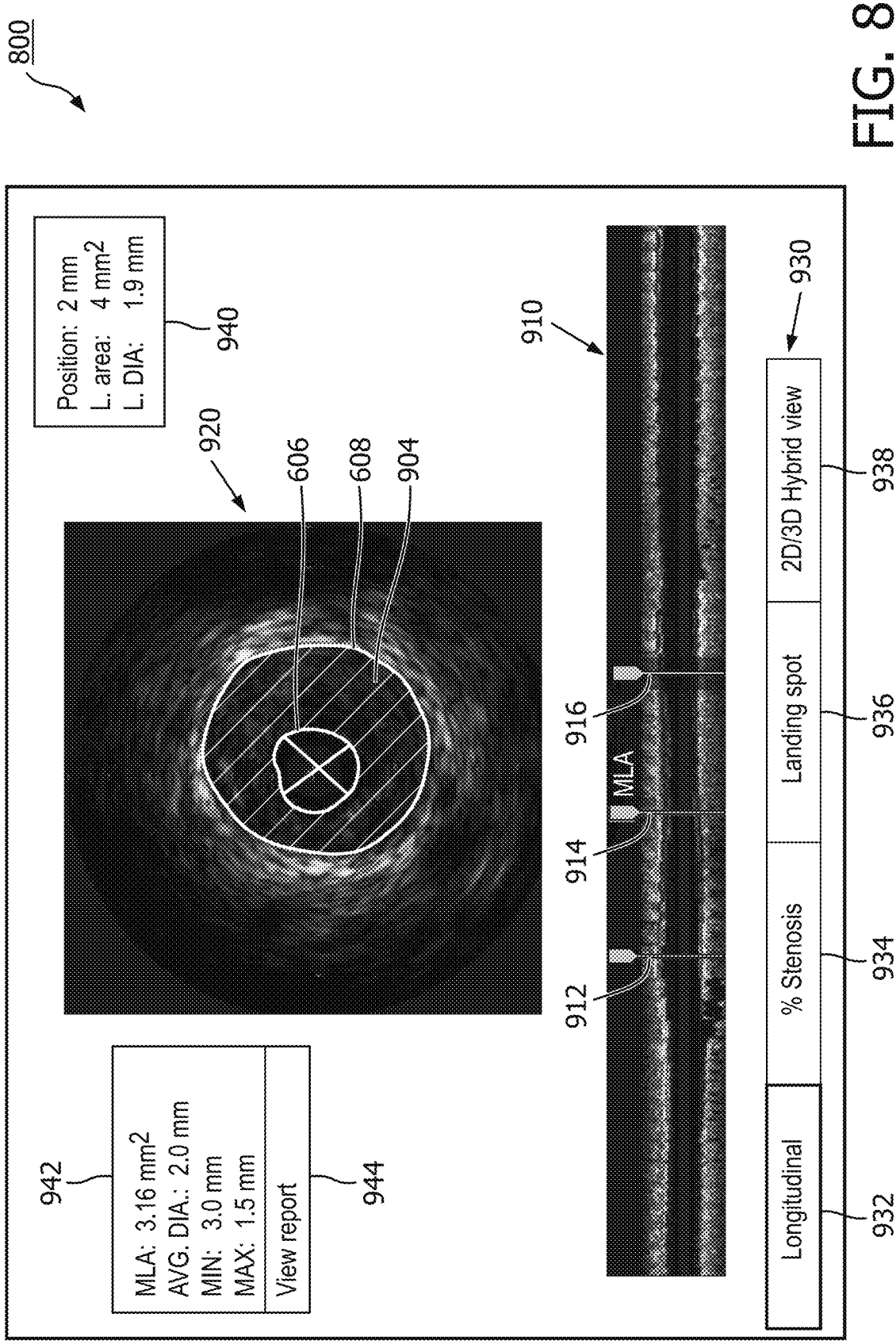
FIG. 8 is an exemplary illustration of a display showing imaging data and automated measurements according to aspects of the present disclosure.
Figure 9:
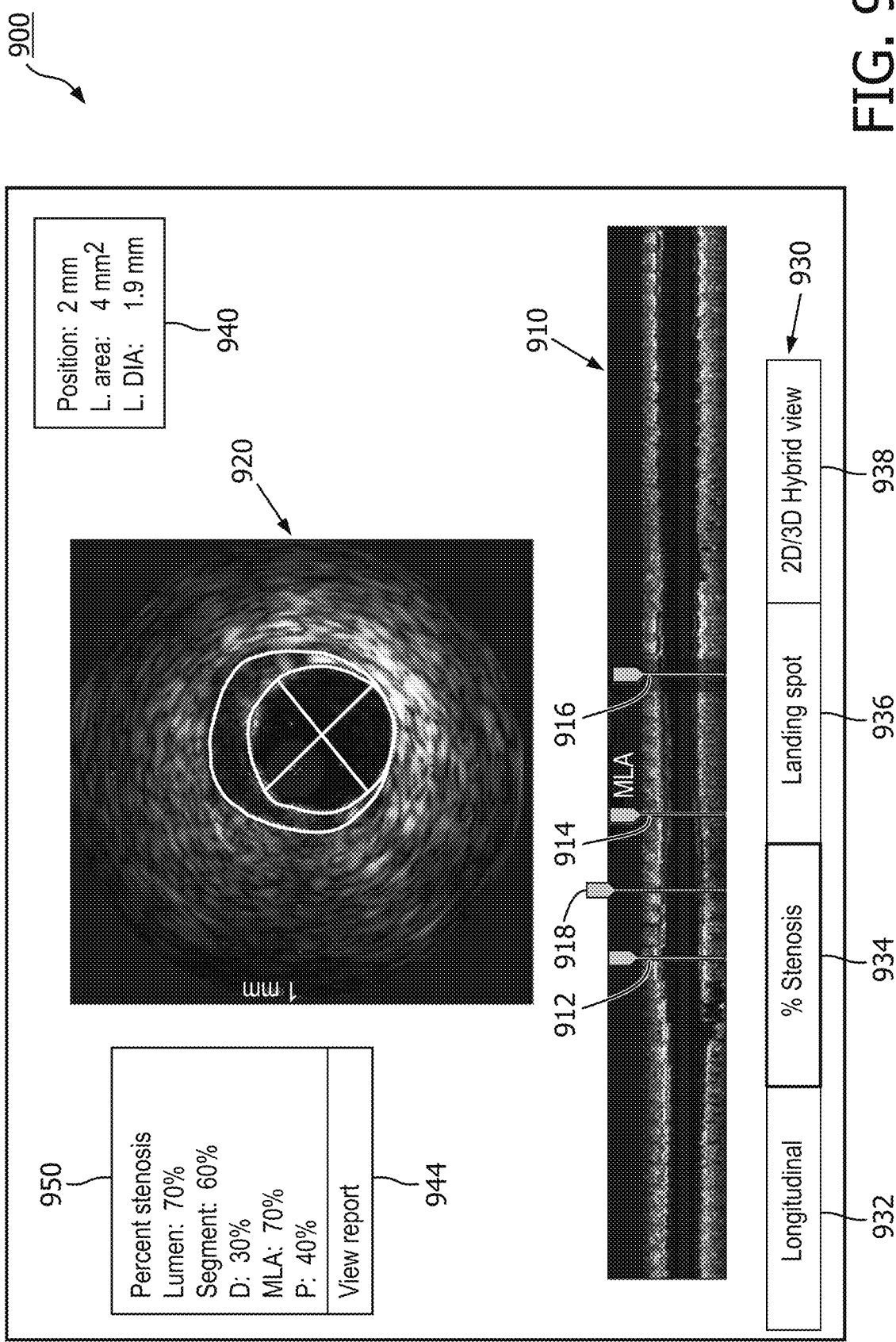
FIG. 9 is an exemplary illustration of another display showing imaging data and measurements according to aspects of the present disclosure.
Figure 10:
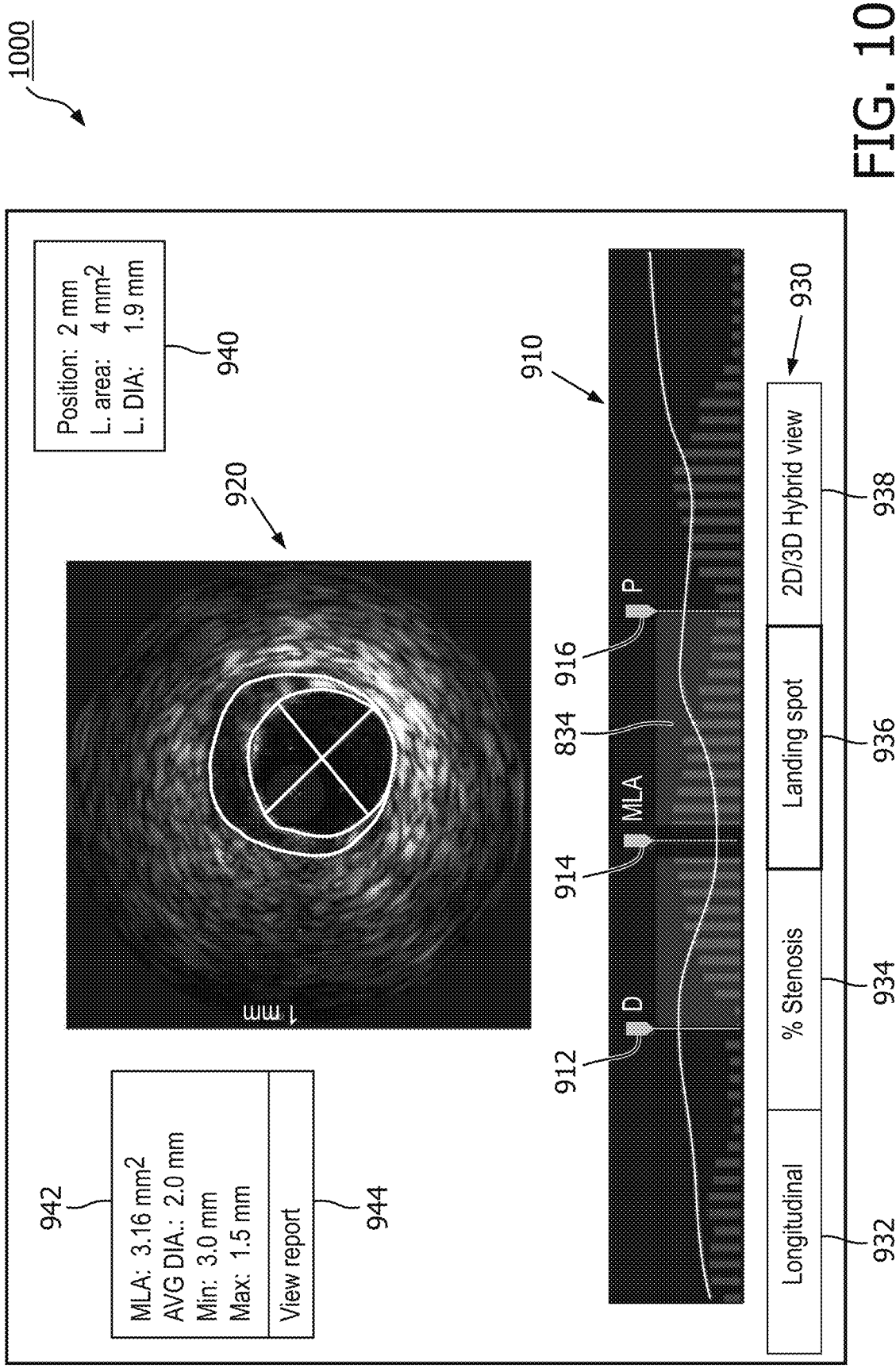
FIG. 10 is an exemplary illustration of another display showing imaging data, landmarks, and measurements according to aspects of the present disclosure.
Figure 11:
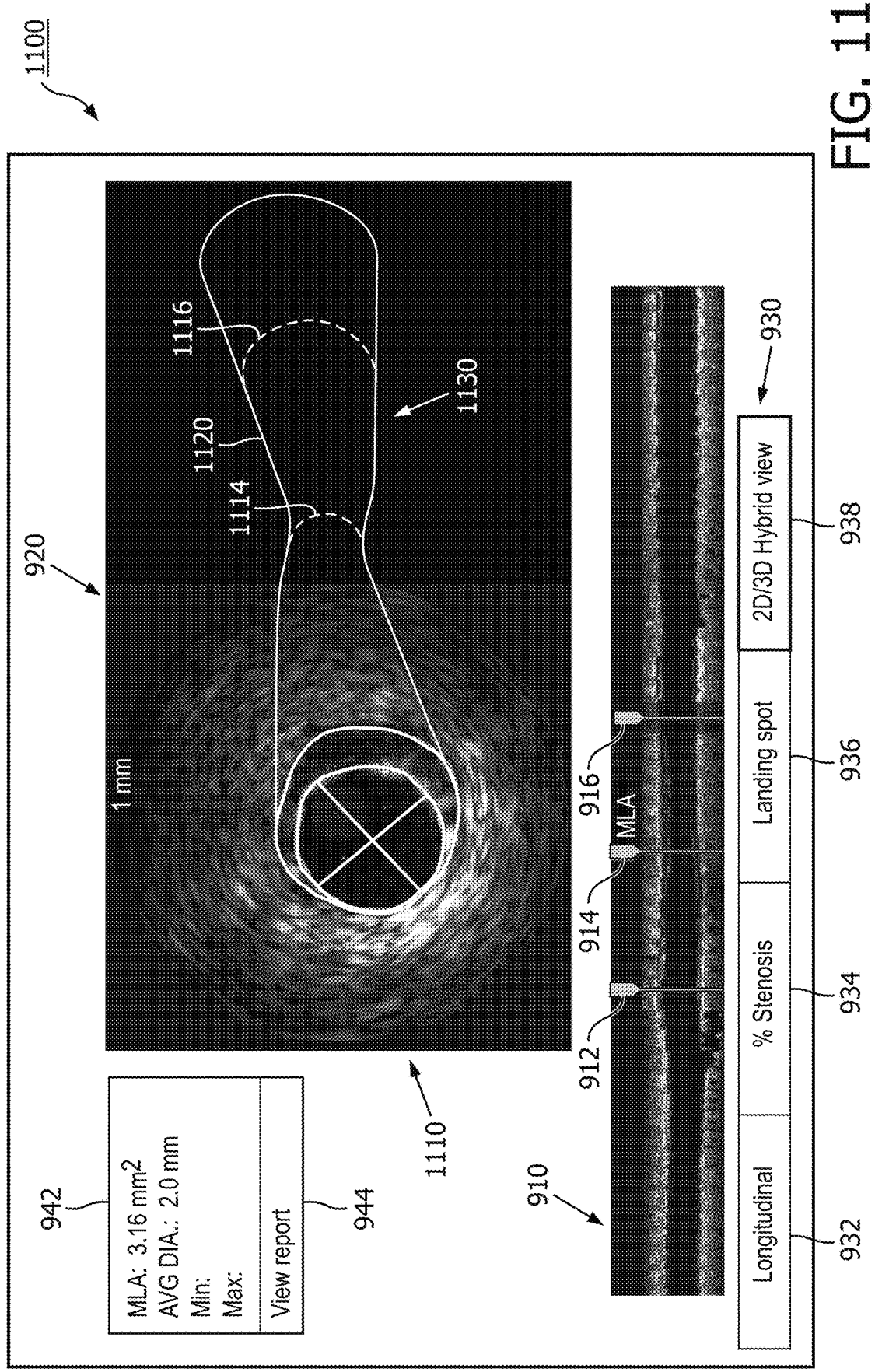
FIG. 11 is an exemplary illustration of another display showing imaging data and measurements according to aspects of the present disclosure.

FIG. 8 shows an exemplary visualization 800 according to aspects of the present disclosure. The visualization 800 may be generated by the system 100 and displayed on a monitor 108. The visualization 800 may include a longitudinal view 910 of a lumen and a transverse view 920 of a lumen. In some embodiments, the views 910, 920 of the lumen include intraluminal imaging data, such as IVUS data received from a device 102 as shown in FIG. 1. The longitudinal view 910 of the lumen may be selected from an option list 930 including a classic longitudinal view 932 (as shown in FIG. 8), a percent stenosis view 934 (as shown in FIG. 9), a landing spot view 936 (as shown in FIG. 10), and a 2D/3D hybrid view 938 (as shown in FIG. 11). The user may select any of the options of the option list 930 to view the corresponding longitudinal view 910. The transverse view 920 may also be referred to a 2D tomographic view, and may correspond to a position along the longitudinal view 910, such as at a minimum lumen area (MLA). Various reference points 912, 914, 916 may be displayed on the longitudinal view 910, including a distal reference point 912, a MLA reference point 914, and a proximal reference point 916.

The system 100 may automatically identify landmarks (or key luminal areas) within the views 910, 920 of the visualization 800. In some embodiments, the system 100 may automatically detect landmarks within each frame of the views 910, 920 and measure the dimensions of these landmarks. For example, the system may automatically detect and measure the diameter of and area within a vessel border 608 and a lumen border 606 of the lumen in the transverse view 910, as well as the length of the lumen in the longitudinal view 920. These measurements may be used to automatically identify one or more lesions within the lumen. For example, the MLA reference point 914 may be identified as a lesion, and the distal and proximal reference points 912, 916 may be identified as a distal and proximal edge of the lesion, respectively.

The area between the vessel border 608 and the lumen border 606 may be shown as highlighted area 904. These automatic measurements may be displayed on the visualization 800, such as in text boxes 940, 942. A user may select a view report icon 944 to view a report including all of the calculated measurements. This icon 944 may be used to automatically store the measurement in file of the patient.

FIG. 9 shows an exemplary visualization 900 according to aspects of the present disclosure. The visualization 900 may be generated by the system 100 and displayed on a monitor 108. The visualization 900 may include a longitudinal view 910 and a transverse (or cross-sectional) view 920 of a lumen. In some embodiments, the longitudinal view 910 may be a percent stenosis longitudinal view 934, such that the system 100 is configured to automatically calculate a percent stenosis across the lumen or a segment of the lumen compared to a reference frame. For example, the system 100 has automatically measured each frame of imaging data in visualization 900 to determine the percent stenosis across the entire lumen as 70% and across the segment between the distal reference point 912 and the proximal reference point 916 as 60% (as shown in text box 950). The visualization 900 may also display the percent stenosis at the distal, MLA, and proximal reference points 912, 914, 916. These features may also be manually adjusted by the user.

In some embodiments, the position of the transverse view 920 may be manually selected by a user. For example, a sliding reference point 918 may be included in the longitudinal view 910 that may show the position of the transverse view 920. The user may slide this sliding reference point 918 to view any position along the length of the lumen. The position of the sliding reference point 918 along the lumen may be displayed in text box 940, as well as the area and diameter of the lumen at the sliding reference point 918.

FIG. 10 shows an exemplary visualization 1000 according to aspects of the present disclosure. The visualization 1000 may be generated by the system 100 and displayed on a monitor 108. The visualization 1000 may include a longitudinal view 910 and a transverse view 920 of a lumen. In some embodiments, the longitudinal view 910 may be a "landing spot" longitudinal view 936, such that the system 100 is configured to automatically identify a lumen and recommend a landing spot for placement of a stent. In the example of FIG. 10, the system 100 has automatically identified an MLA reference point 914 as the center of a lesion within the lumen. The visualization 1000 includes a recommended landing spot 834 based on the position of the detected lesion. The edges of the recommended landing spot 834 may be marked by distal and proximal reference points 912, 916. These points 912, 916 may be manually adjusted by the user.

FIG. 11 shows an exemplary visualization 1100 according to aspects of the present disclosure. The visualization 1100 may be generated by the system 100 and displayed on a monitor 108. The visualization 1100 may include a longitudinal view 910 and a 2D/3D hybrid view 1110. In some embodiments, a user is able to select the 2D/3D hybrid view option 938, or use a control button or handle to display the 2D/3D hybrid view 1110 on the monitor 108. In some embodiments, a transverse view 920 (or 2D tomographic view), such as that shown in FIGS. 5-10, may be used to generate the 2D/3D hybrid view 1110 based on a selection of the user. The 2D/3D hybrid view 1110 may be generated by the system 100 by combining measurements of the lumen or vessel borders from a plurality of image frames. In some embodiments, the 2D/3D hybrid view 1110 is generated using 500-2,500 image frames. In other embodiments, the 2D/3D hybrid view 1110 is generated using 10-100 image frames, 200-500 image frames, 500-1,000 image frames, 1,000-2,000 image frames, or 5,000-10,000 image frames. In some embodiments, the 2D/3D hybrid view 1110 includes a transverse view 920 of the lumen and a 3D portion 1130 extending out from the transverse view 920. The 2D/3D hybrid view 1110 may include a lumen border 1120 in the transverse view 920 and extending into the 3D portion 1130 of the view 1110. The 2D/3D hybrid view 1110 may include indicators 1114, 1116 corresponding to positions on the longitudinal view 910 (such as the MLA reference point 914 and the proximal reference point 916). The 2D/3D hybrid view 1110 may also include any of key luminal areas or landmarks as discussed above. In some embodiments, the 2D/3D hybrid view 1110 may rotated or enlarged by a user to view different regions of the lumen. The user may also select different positions along the longitudinal view 910 as the starting point of the 2D/3D hybrid view (such as showing a transverse view 920 corresponding to the MLA or distal reference points 914, 916). The 2D/3D hybrid view 1110 may provide a user a view of imaging data along the length of the lumen that is easy to understand.

Figure 12:
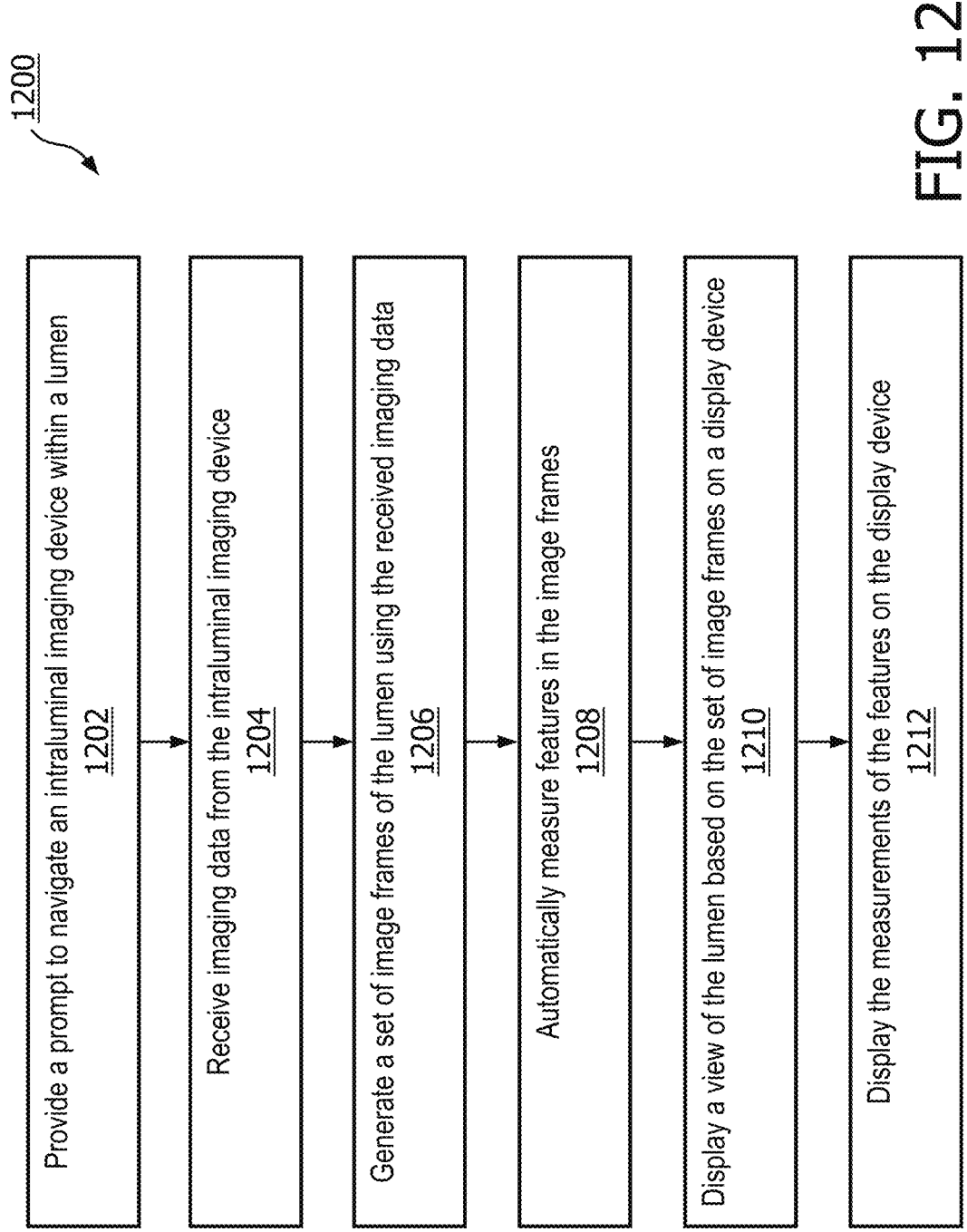
FIG. 12 is a flow diagram of a method of measuring and displaying features in a lumen according to aspects of the present disclosure.

FIG. 12 is a flow diagram of a method 1200 of providing intraluminal imaging to measuring and display features in a lumen to a user. In some embodiments, the steps of the method 1200 may be carried out by the intraluminal imaging system 100 and associated components as shown in FIG. 1 and any of the displays as shown in FIGS. 5-11. It is understood that the steps of method 1200 may be performed in a different order than shown in FIG. 12, additional steps can be provided before, during, and after the steps, and/or some of the steps described can be replaced or eliminated in other embodiments.

At step 1202, the method 1200 may include providing a prompt to navigate an intraluminal imaging device within a lumen. The intraluminal imaging device may be the intraluminal imaging device 102 as shown in FIG. 1. The prompt may include navigating the intraluminal imaging device to a starting point in the lumen, as well as activating sensors in the intraluminal device. This prompt may be presented with text as well as images showing where the user should place the intraluminal device.

At step 1204, the method 1200 may include receiving imaging data from the intraluminal device. This imaging data may help a user to accurately navigate the intraluminal device according to the prompt of step 1202. For example, if the prompt of step 1202 directs the user to navigate the intraluminal device from a distal end of the lumen to a proximal end of the lumen, the imaging data may show imaging data from the intraluminal device as it is moved through the lumen. In some embodiments, the imaging data may include IVUS data showing the layers of tissue on the interior of the lumen. In other embodiments, the imaging data includes data from another modality such as angiographic image data. This data may be used to compile an angiographic image of the lumen. Thus, the imaging data may help the user to accurately perform the operation outlined in the prompt.

At step 1206, the method 1200 may include generating a set of image frames of the lumen using the received imaging data. In some embodiments, the set of image frames are IVUS images showing 2D tomographic image slices of the lumen (i.e., showing a transverse view of the lumen), as shown in FIGS. 5-11. In other embodiments, the image frames are generated with another imaging modality, such as OCT, ICE, FLICE, ultrasound, fluoroscopy, radiography, angiography, other medical imaging modalities, or combinations thereof. Each image frame may be correlated to a particular location along the length of the lumen.

At step 1208, the method 1200 may include automatically measuring features in the image frames. A controller of the system may automatically identify and measure these features based on imaging data. The measured features in the image frames may include anatomical features such as tissue boundaries (such as lumen and vessel boundaries), lesions, aneurisms, bifurcations, as well as manmade features such as stents. The automatic measurements may include lumen or vessel diameter, lumen or vessel area, lumen or vessel eccentricity, center measurements of the lumen or vessel, lumen or vessel boundary thickness, pressure measurements, percent stenosis, malapposition areas, landing spots, and other measurements performed by the controller. In some embodiments, the system identifies a lesion within the lumen and automatically measures at least three points of the lesion: a proximal reference point, a distal reference point, and a MLA. In some embodiments, the controller identifies the features based on variations in the imaging data, such as changes in brightness, speckle patterns, regions with similar shapes, linear or curved features, as well as other variations. In some embodiments, the controller identifies the features based on previous user testing, clinical trials, published guidelines, and consensus in the medical field. The automatic measurements of the system may be manually adjusted or edited by the user. For example, the user may change a lumen boundary to correct an error in measurement.

At step 1210, the method 1200 may include displaying a view of the lumen based on the set of image frames on a display device. The display device may be a monitor 108 as shown in FIG. 1. The view of the lumen may include a transverse, longitudinal, and/or 2D/3D hybrid view of the lumen, such as those shown in FIGS. 5-11. In some embodiments, two or more views of the lumen are shown on a same screen of the display device. For example, a transverse intraluminal view of the lumen may be shown with a longitudinal view of the lumen. A 2D/3D hybrid view of the lumen may be shown with a transverse view at one end, as shown in FIG. 11. In some embodiments, a segment of the lumen is shown head-on (i.e., a transverse view) to assess various frames of the lumen and a separate cross-sectional display (i.e., longitudinal view) is displayed adjacent to the head-on view. The views of the lumen may be visually correlated, such that a user can easily understand which portions of the lumen are being displayed. In some embodiments, the views may be visually correlated by similar colors, patterns, indicators, or symbols. This correlation may help a user to more easily understand the context for each view displayed on the display device. The user may be able to access other views on the display by selecting areas of the displayed views. For example, the user may scroll through the various image frames of the lumen by sliding an indicator along a longitudinal view of the lumen. Furthermore, the display may show a 2D/3D hybrid view of the lumen and the user may be able to select various positions along the 3D extension of the view to access 2D transverse views at the selected positions. In some embodiments, the user is presented with selectable options to view various longitudinal views of the lesion including a classic longitudinal view (such as that shown in FIG. 8), a percent stenosis longitudinal view (such as that shown in FIG. 9), a landing spot longitudinal view (such as that shown in FIG. 10), and a 2D/3D hybrid view (such as that shown in FIG. 11). The user may toggle through these options and view transverse views corresponding to locations on the various longitudinal views.

At step 1212, the method 1200 may include displaying the measurements of the features on the display device. In some embodiments, the measurements are shown with highlighted lines or regions. For example, vessel and lumen boundaries may be marked with colored lines as shown in FIGS. 6-11 and the area between these boundaries may be highlighted as shown in FIG. 8. In some embodiments, the user may select certain regions in the displayed images to highlight the regions or display the measurements. The measurements may be shown on a single screen with one or more views of the vessel. For example, the measurements may be shown in one or more text boxes such as boxes 940, 942, and 950 shown in FIGS. 8-11 and/or directly on the one or more views of the lumen. In some embodiments, the display device is configured to display a transverse view of the lumen, a longitudinal view of the lumen, and the measurements of anatomical features of the lumen on a single screen. In some Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal medical imaging system, comprising:
 a controller in communication with an intraluminal imaging device configured to be positioned within a body lumen of a patient, the controller configured to:
  receive imaging data from the intraluminal imaging device as the intraluminal imaging device is moved through the body lumen;
  generate a plurality of image frames using the received imaging data;
  automatically identify a lumen border in each of the plurality of image frames; and
  generate a longitudinal outline of the body lumen based on the identified lumen border in the plurality of image frames; and
 a display device in communication with the controller and configured to display, on a single screen:
  the longitudinal outline of the body lumen; and
  a first image frame of the plurality of image frames,
  wherein the first image frame comprises an outline of the lumen border in the first image frame,
  wherein the first image frame corresponds to a first location along the longitudinal outline,
  wherein a position of the first image frame within the single screen is representative of the first location such that the outline of the lumen border in the first image frame is a portion of the longitudinal outline at the corresponding first location, and
  wherein the first image frame and the longitudinal outline form a hybrid two-dimensional/three-dimensional representation in which the longitudinal outline extends from the first image frame.

2. The intraluminal medical imaging system of claim 1, wherein the first image frame is a two-dimensional tomographic image of the body lumen.

3. The system of claim 1,
wherein the controller configured to automatically calculate a luminal area associated with the body lumen for each of the plurality of image frames, and
wherein the single screen further comprises:
the calculated luminal area corresponding to the first image frame; and
a longitudinal view of the body lumen distinct from the longitudinal outline.

4. The intraluminal medical imaging system of claim 3, wherein a location of the first image frame within the body lumen is displayed on the longitudinal view of the body lumen.

5. The intraluminal medical imaging system of claim 1, wherein the display device is further configured to display an area of interest including a lesion.

6. The intraluminal medical imaging system of claim 5, wherein the display device is further configured to display, on the single screen, a percentage of narrowing of the body lumen within the area of interest.

7. The intraluminal medical imaging system of claim 3, wherein the controller is further configured to automatically determine an optimal location for a stent based on the received image data.

8. The intraluminal medical imaging system of claim 7, wherein the display device is further configured to display the optimal location on the longitudinal view of the body lumen.

9. The system of claim 3, wherein the longitudinal view of the body lumen includes a stylized graphic comprising:
a plot of the calculated luminal area for each of the plurality of image frames.

10. The system of claim 3, wherein the longitudinal view of the body lumen includes a stylized graphic comprising:
a plot of plaque burden measurements for each of the plurality of image frames.

11. The system of claim 3, wherein the longitudinal view of the body lumen further comprises:
a first graphic element identifying a location corresponding to a proximal landing zone for a stent; and
a second graphic element identifying a location corresponding to a distal landing zone for the stent.

12. The system of claim 1, wherein the longitudinal outline of the body lumen is overlaid over the first image frame.

13. The system of claim 1, wherein the lumen border in the first image frame forms an end of the longitudinal outline of the body lumen.

14. A method of intraluminal medical imaging, comprising:
receiving, with a controller in communication with an intraluminal imaging device positioned within a body lumen of a patient, imaging data associated with the body lumen as the intraluminal imaging device is moved through the body lumen;
generating, with the controller, a plurality of image frames using the received imaging data:
automatically identifying, with the controller, a lumen border in each of plurality of image frames;
generating a longitudinal outline of the body lumen based on the identified lumen border in the plurality of image frames; and
displaying, on a single screen of a display device:
the longitudinal outline of the body lumen; and
a first image frame of the plurality of image frames,
wherein the first image frame comprises an outline of the lumen border in the first image frame,
wherein the first image frame corresponds to a first location along the longitudinal outline,
wherein a position of the first image frame within the single screen is representative of the first location such that the outline of the lumen border in the first image frame is a portion of the longitudinal outline at the corresponding first location, and
wherein the first image frame and the longitudinal outline form a hybrid two-dimensional/three-dimensional representation in which the longitudinal outline extends from the first image frame.

15. The method of claim 14, wherein the first image frame is a two-dimensional tomographic image of the body lumen.

16. The method of claim 14,
further comprising automatically calculating, with the controller, a luminal area associated with the body lumen for each of the plurality of image frames, and
wherein the single screen further comprises
the calculated luminal area corresponding to the first image frame; and
a longitudinal view of the body lumen distinct from the longitudinal outline.

17. The method of claim 16, wherein a location of the first image frame within the body lumen is displayed on the longitudinal view of the body lumen.

18. The method of claim 14, further comprising displaying, on the single screen of the display device, an area of interest within the body lumen including a lesion.

19. The method of claim 18, further comprising displaying, on the single screen of the display device, a percentage of narrowing of the body lumen within the area of interest.

20. The method of claim 16, further comprising determining, with the controller, an optimal location for a stent based on the received image data.

21. The method of claim 20, further comprising displaying the optimal location on the longitudinal view of the body lumen.

* * * * *